United States Patent
Kim

(10) Patent No.: US 9,543,946 B2
(45) Date of Patent: Jan. 10, 2017

(54) SIGNAL PROCESSING DEVICE WITHOUT MECHANICAL SWITCH FOR ON/OFF OPERATION

(71) Applicant: Samsung Electronics Co., Ltd., Suwon-si (KR)

(72) Inventor: Jong Pal Kim, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 260 days.

(21) Appl. No.: 14/063,683

(22) Filed: Oct. 25, 2013

(65) Prior Publication Data

US 2014/0145784 A1 May 29, 2014

(30) Foreign Application Priority Data

Nov. 23, 2012 (KR) .................. 10-2012-0133524

(51) Int. Cl.
*H03K 17/96* (2006.01)

(52) U.S. Cl.
CPC .......... *H03K 17/96* (2013.01); *H03K 17/9645* (2013.01); *A61B 2560/0204* (2013.01)

(58) Field of Classification Search
CPC ............... H03K 17/96; H03K 17/9645; A61B 2560/0204; A61B 5/0006; A61B 5/0404; A61B 5/0452; A61B 5/0402; A61B 5/0245; A61B 5/681; A61B 5/04525; G06F 17/00
See application file for complete search history.

(56) References Cited

U.S. PATENT DOCUMENTS

| | | | | |
|---|---|---|---|---|
| 4,938,228 A * | 7/1990 | Righter | ................ | A61B 5/0245 600/503 |
| 5,191,891 A * | 3/1993 | Righter | ................ | A61B 5/0404 600/508 |
| 5,289,824 A * | 3/1994 | Mills | .................... | A61B 5/0404 128/904 |
| 5,862,803 A * | 1/1999 | Besson | .............. | A61B 5/14552 128/903 |
| 6,441,747 B1 * | 8/2002 | Khair | ................... | A61B 5/0006 128/903 |

(Continued)

FOREIGN PATENT DOCUMENTS

| CN | 101965151 A | 2/2011 |
|---|---|---|
| EP | 0 170 448 A2 | 2/1986 |

(Continued)

OTHER PUBLICATIONS

Extended European Search Report issued Mar. 5, 2014 in counterpart European Patent Application No. 13186566.9. (12 pages in English).

(Continued)

*Primary Examiner* — Jaweed A Abbaszadeh
*Assistant Examiner* — Brian J Corcoran
(74) *Attorney, Agent, or Firm* — NSIP Law

(57) ABSTRACT

A signal processing device includes a detection unit configured to detect an intent to use the signal processing device based on whether the signal processing device is in contact with a subject; and a power supply unit configured to supply power to operate the signal processing device based on the detected intent to use the signal processing device without using a separate ON/OFF switch to supply the power to operate the signal processing device.

19 Claims, 10 Drawing Sheets

(56) References Cited

U.S. PATENT DOCUMENTS

| | | | |
|---|---|---|---|
| 6,950,695 B2* | 9/2005 | Chen | A61B 5/02438 600/509 |
| 6,961,601 B2* | 11/2005 | Matthews | A61B 5/0408 600/372 |
| 7,583,826 B2 | 9/2009 | Nakamura et al. | |
| 8,467,861 B2* | 6/2013 | Rytky | A61B 5/02438 600/509 |
| 2004/0021786 A1 | 2/2004 | Nakamura et al. | |
| 2004/0073127 A1 | 4/2004 | Istvan et al. | |
| 2008/0139953 A1* | 6/2008 | Baker | A61B 5/0006 600/509 |
| 2008/0195169 A1* | 8/2008 | Pinter | A61B 5/0424 607/28 |
| 2008/0287769 A1* | 11/2008 | Kurzweil | A61B 5/0408 600/388 |
| 2008/0288026 A1* | 11/2008 | Cross | A61B 5/0408 607/60 |
| 2011/0021937 A1* | 1/2011 | Hugh | A61B 5/0006 600/523 |
| 2011/0159864 A1 | 6/2011 | Park et al. | |

FOREIGN PATENT DOCUMENTS

| | | |
|---|---|---|
| JP | 11-188013 A | 7/1999 |
| JP | 2000-157634 A | 6/2000 |
| JP | 2001-198096 A | 7/2001 |
| JP | 2003-304147 A | 10/2003 |
| JP | 2009-82362 A | 4/2009 |
| KR | 1985-0002650 A | 5/1985 |
| KR | 2003-0041387 A | 5/2003 |
| KR | 2003-0084379 A | 11/2003 |
| KR | 10-2008-0063932 A | 7/2008 |
| KR | 10-2009-0027371 A | 3/2009 |
| WO | WO 2010/038156 A1 | 4/2010 |
| WO | WO 2011/132129 A1 | 10/2011 |

OTHER PUBLICATIONS

Chinese Office Action issued on Feb. 19, 2016 in counterpart Chinese Application No. 201310497299.1. (20 pages with English translation).

* cited by examiner

SIGNAL PROCESSING DEVICE WITHOUT MECHANICAL SWITCH FOR ON/OFF OPERATION

CROSS-REFERENCE TO RELATED APPLICATIONS

This application claims the benefit under 35 USC 119(a) of Korean Patent Application No. 10-2012-0133524 filed on Nov. 23, 2012, in the Korean Intellectual Property Office, the disclosure of which is incorporated herein by reference in its entirety for all purposes.

BACKGROUND

1. Field

This application relates to a signal processing device without a mechanical switch for an ON/OFF operation.

2. Description of Related Art

A small amount of electric current is in constant flow through a human body since the human body is a conductive material. Accordingly, various physiological characteristics may be measured by sensing an electric current or a change in the electric current caused by an external stimulation applied to a human body.

This principle enables a biopotential to be measured. Examples of a biopotential include an electrocardiography (ECG) potential, an electromyography (EMG) potential, an electroencephalography (EEG) potential, a galvanic skin response (GSR), electrooculography (EOG), a body temperature, a pulse, a blood pressure, and a body motion. A signal processing device is used to sense a biometric signal or a change in a biometric signal.

SUMMARY

In one general aspect, a signal processing device includes a detection unit configured to detect an intent to use the signal processing device based on whether the signal processing device is in contact with a subject; and a power supply unit configured to supply power to operate the signal processing device based on the detected intent to use the signal processing device without using a separate ON/OFF switch to supply the power to operate the signal processing device.

The detection unit may include two first electrical contacts configured to be in contact with the subject or a first conductive member when the signal processing device is in contact with the subject; the power supply unit may be further configured to supply the power to operate the signal processing device based on whether the two first electrical contacts are in contact with the subject or the first conductive member; and the signal processing device may further include a circuit unit configured to receive a signal from the subject in response to the power to operate the signal processing device supplied by the power supply unit, and process the received signal.

The signal processing device may further include at least two second electrical contacts configured to receive the signal from the subject, and supply the signal received from the subject to the circuit unit.

The signal processing device may further include an electrode unit configured to be in contact with the subject, and the electrode unit may include the first conductive member, and at least two second conductive members configured to be in contact with at least three regions of the subject to receive the signal from the subject.

The electrode unit may further include contacts connected to the at least two second conductive members to receive the signal from the subject from the at least two second conductive members; and the at least two second electrical contacts may be configured to be in contact with the contacts connected to the at least two second conductive members to receive the signal from the subject from the contacts connected to the at least two second conductive members when the signal processing device is in contact with the subject.

The first conductive member may be configured not to be in contact with the subject when the electrode unit is in contact with the subject.

The power supply unit may be further configured to generate a bias voltage separate from the power to operate the signal processing unit; the power supply unit may further include an enable terminal; the first conductive member may be one of the at least two second conductive members; the electrode unit may further include a contact connected to the one of the at least two second conductive members that is the first conductive member; the at least two first electrical contacts may include a first contact supplied with the bias voltage, and a second contact connected to the enable terminal of the power supply unit; and the bias voltage may be supplied to the enable terminal of the power supply unit based on whether the first contact and the second contact are in contact with the contact connected to the one of the at least two second conductive members that is the first conductive member.

The power supply unit may include a state determining unit configured to generate a control signal for controlling the power supply based on a voltage supplied to the state determining unit based on whether the two first electrical contacts are in contact with the subject or the first conductive member, and a power output unit configured to receive battery power from a battery, generate the power to operate the signal processing device based on the battery power, and selectively supply the power to operate the signal processing device to the circuit unit based on the control signal; and the power to operate the signal processing device generated by the power output unit may be the battery power or a power having a voltage that is different from a voltage of the battery power.

The state determining unit may include an enable terminal configured to receive the voltage supplied to the state determining unit; a switching unit configured to generate a control signal for controlling the power supply based on the voltage received by the enable terminal based on whether the two first electrical contacts are in contact with the subject or the first conductive member; and a pull-down resistor connected to the enable terminal to prevent a voltage on the enable terminal from floating.

The at least two first electrical contacts may include a first contact connected to the battery, and a second contact connected to the enable terminal of the state determining unit; and the battery power may be supplied from the battery to the enable terminal of the state determining unit based on whether the first contact and the second contact are in contact with the subject or the first conductive member.

The power output unit may be further configured to generate a bias voltage separate from the battery power; the at least two first electrical contacts may include a first contact supplied with the bias voltage, and a second contact connected to the enable terminal of the state determining unit; and the bias voltage may be supplied to the enable terminal of the state determining unit based on whether the first contact and the second contact are in contact with the subject or the first conductive member.

The state determining unit may include an enable terminal configured to receive the voltage supplied to the state determining unit; an input comparing unit configured to generate the control signal by comparing the voltage received by the enable terminal with a threshold voltage based on whether the two first electrical contacts are in contact with the subject or the first conductive member; and a threshold voltage generating unit including a voltage divider having a resistance ratio, the threshold voltage generating unit being configured to generate the threshold voltage based on the resistance ratio of the voltage divider.

The two first electrical contacts may include a first contact connected to the battery, and a second contact connected to the enable terminal of the state determining unit; and the power may be supplied from the battery to the enable terminal of the state determining unit based on whether the first contact and the second contact are in contact with the subject or the first conductive member.

The two first electrical contacts may include a first contact configured to receive the bias voltage generated by the power output unit, and a second contact connected to the enable terminal of the state determining unit; and the bias voltage may be supplied to the enable terminal of the state determining unit based on whether the first contact and the second contact are in contact with the subject or the first conductive member.

The voltage divider may be configured to receive the battery power from the battery, or the power to operate the signal processing device from the power output unit.

The signal processing device may further include a pull-down resistor or a pull-up resistor connected to the enable terminal to prevent a voltage on the enable terminal from floating.

The power supply unit may be further configured to receive an input power and a ground power from a battery.

In another general aspect, a signal processing device includes an electrode unit configured to contact a subject, the electrode unit including a first conductive member configured not to be in contact with the subject when the electrode unit is in contact with the subject, and at least two second conductive members configured to be in contact with at least three regions of the subject to receive a signal from the subject; the signal processing device further including two first electrical contacts configured to be in contact with the first conductive member; at least three second electrical contacts configured to receive the signal from the subject; and a circuit unit configured to receive the signal through the at least three second electrical contacts in response to power supplied to the circuit unit from a battery based on whether the two first electrical contacts are in contact with the first conductive member, and process the received signal.

The two first electrical contacts may include a first contact connected to the battery, and a second contact connected to the circuit unit; and the power may be supplied to the circuit unit from the battery through contacts between the first and second contacts and the first conductive member.

The signal processing device may further include contacts connected to the at least two second conductive members; and the signal may be received through the at least three second electrical contacts in contact with the contacts connected to the at least two second conductive members.

Other features and aspects will be apparent from the following detailed description, the drawings, and the claims.

DETAILED DESCRIPTION

Figure 1:
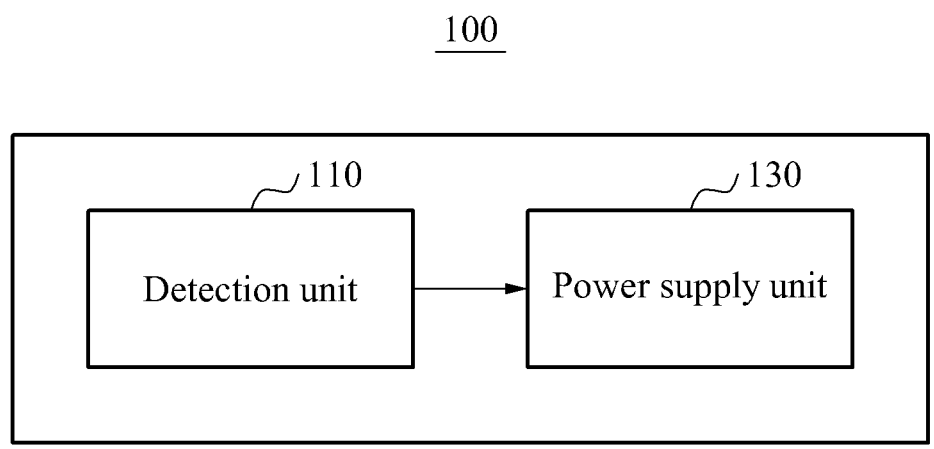
FIG. 1 is a diagram illustrating an example of a signal processing device.

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of steps necessarily occurring in a certain order. Also, description of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

FIG. 1 is a diagram illustrating an example of a signal processing device 100. Referring to FIG. 1, the signal processing device 100 includes a detection unit 110 and a power supply unit 130.

The detection unit 110 detects an intent to use the signal processing device 100 based on whether the signal processing device 100 is in contact with a subject. When a contact of the signal processing device 100 is in contact with a skin of the subject, the detection unit 110 may determine that the subject intends to use the signal processing device 100. As an example, the signal processing device 100 may be a wearable medical device.

In addition to direct surface contact between the signal processing device 100 and the subject, the detection unit 110 may detect the intent to use the signal processing device 100 via an electrode inserted between the subject and the detection unit 110.

The power supply unit 130 supplies power to operate the signal processing device 100 based on the intent to use the signal processing device 100 detected by the detection unit without a separate mechanical switch for an ON/OFF operation of the signal processing unit 100.

Conventionally, a mechanical switch is used to turn an electrocardiography (ECG) sensor ON and OFF. However, the use of such a switch may hinder minimization of a device in which the corresponding sensor is included.

Accordingly, the signal processing device 100 may achieve minimization and improve a user convenience by constructing the power supply to operate the signal processing device 100 based on the intent to use the signal processing unit 100 detected by the detection unit 110 in which a separate mechanical switch for an ON/OFF operation is absent.

Figure 2:
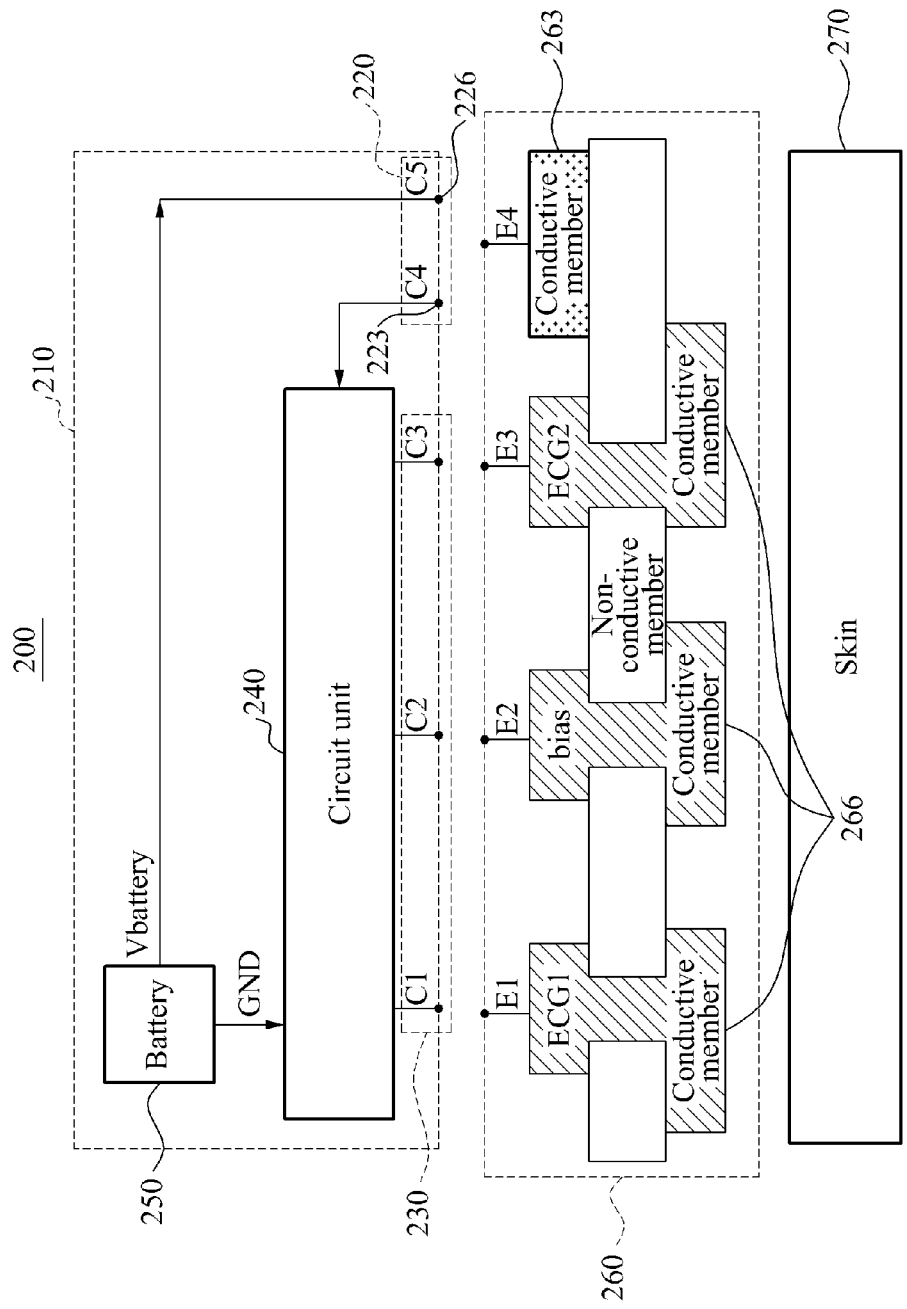
FIG. 2 is a diagram illustrating another example of a signal processing device.

FIG. 2 is a diagram illustrating another example of a signal processing device 200. Referring to FIG. 2, the signal processing device 200 includes a sensor unit 210 and an electrode unit 260. When the sensor unit 210 is connected to the electrode unit 260, the signal processing device 200 supplies power to a circuit unit 240 through a conductive member 263 of the electrode unit 260 to allow the circuit unit 240 to receive a biometric signal from a subject and process the biometric signal.

The sensor unit 210 includes two first electrical contacts C4 and C5 220, at least two second electrical contacts C1, C2, and C3 230, the circuit unit 240, and a battery 250.

The two first electrical contacts C4 and C5 220 may be in contact with the first conductive member 263, which is disposed so that the conductive member 263 is not in non-contact with the subject. The two first electrical contacts C4 and C5 220 include a first contact 226 connected to the battery 250 and a second contact 223 connected to the circuit unit 240. Battery power $V_{battery}$ is supplied to the first contact 226 connected to the battery 250, and is supplied to the circuit unit 240 through the second contact 223 in contact with an electrical contact E4 connected to the first conductive member 263.

The at least two second electrical contacts C1, C2, and C3 230 are connected to the circuit unit 240, and may be in contact with electrical contacts E1, E2, and E3 connected to at least two second conductive members 266 of the electrode unit 260 through which the biometric signal may be received from the subject.

The signal processing device 200 may receive a signal from the subject and process the received signal, and may transmit a signal to the subject through electrical contacts. As used herein, it should be understood that "signal processing" may include providing a signal to a human body as well as receiving a signal from the human body and processing the received signal.

When the first contact 223 and the second contact 226 are not in contact with the electrical contact E4 due to the circuit unit 240 and the electrode unit 260 being disconnected, a power supply to the circuit unit 240 is interrupted so the circuit unit 240 does not operate.

The electrode unit 260 includes the first conductive member 263 and the at least two second conductive members 266 disposed to be in contact with at least three regions of the subject through which the biometric signal may be received from the subject.

When the first conductive member 263 is in contact with the first contact 223 and the second contact 226, the battery power $V_{battery}$ is supplied to the circuit unit 240 to enable the circuit 240 to receive the biometric signal from the electrode unit 260 through the at least two second electrical contacts C1, C2, and C3 230 and process the biometric signal.

The battery power $V_{battery}$ is supplied to the circuit unit 240 automatically through the first conductive member 263 when the circuit unit 240 is in contact with the electrode unit 260, enabling the sensor unit 210 to operate.

When the circuit unit 240 is connected to the electrode unit 260, the electrical contacts E1, E2, and E3 connected to the second conductive members 266 of the electrode unit 260 are in contact with the second electrical contacts C1, C2, and C3 230 of the circuit unit 240, respectively. Also, the first electrical contacts C4 and C5 220 are in contact with the electrical contact E4 connected to the first conductive member 263 of the electrode unit 260.

The electrical contact E4 connecting the first contact 223 to the second contact 226 of the sensor unit 210 may be formed on the first conductive member 263 of the electrode unit 260 that is not in contact with a skin 270 of the subject.

The electrode unit 260 may have one surface physically connected to the circuit unit 240 to establish an electrical connection with the circuit unit 240 and another surface connected to the skin 270 through the second conductive members 266 through which the biometric signal may be received from the subject.

The electrode unit 260 may receive a biometric signal ECG1, for example, from a part of the skin 270 through a connection between the electrical contacts C1 and E1, and may receive a biometric signal ECG2, for example, from another part of the skin 270 through a connection between the electrical contacts C3 and E3. The circuit unit 240 may measure the biometric signals ECG1 and ECG2 by differentially amplifying the biometric signals ECG1 and ECG2.

As an example, the signal processing device 200 may be a wearable medical device, may receive the biometric signal from the subject through connection between the sensor unit 210 and the electrode unit 260, and may process the biometric signal.

The physical connection between the electrical contacts of the sensor unit 210 and the electrode unit 260 may be implemented in various ways, for example, as a snap-type point-to-point contact, a surface-to-surface contact, a socket-assisted contact, and any other type of contact known to one of ordinary skill in the art. Also, an electrically identical point may be implemented as at least two physically different elements.

Although not shown in FIG. 2, an adhesive element may be used to improve the connection between the sensor unit 210 and the electrode unit 260, or between the electrode unit 260 and the skin 270. For example, a non-conductive adhesive material may be applied or a double-sided adhesive tape may be attached to a portion or an entirety of a non-conductive member of the electrode unit 260 disposed to be in contact with the circuit unit 240.

The signal processing device 200 may output or apply an electric current to the subject or provide an electrical stimulation to the subject as well as receiving the biometric signal from the subject.

Figure 3:
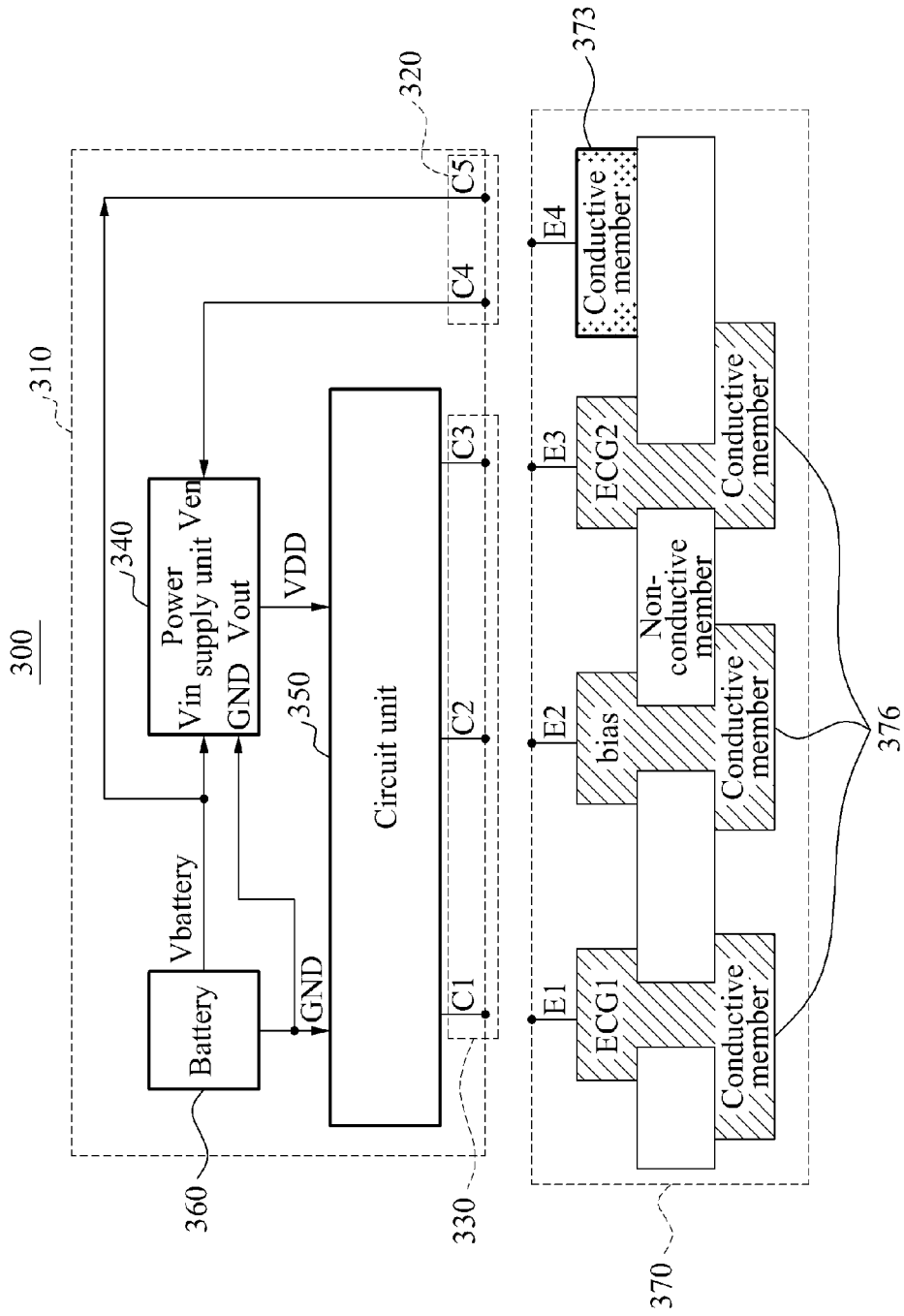
FIG. 3 is a diagram illustrating another example of a signal processing device.

FIG. 3 is a diagram illustrating another example of a signal processing device 300. Referring to FIG. 3, the signal processing device 300 includes a sensor unit 310 and an electrode unit 370. The signal processing device 300 supplies power to a power supply unit 340 through a first conductive member 373 of the electrode unit 370.

Similar to the signal processing unit 200 of FIG. 2, the signal processing unit 300 may determine whether the sensor unit 310 is in contact with the electrode unit 370 via the first conductive member 373 of the electrode unit 370 when the sensor unit 310 is connected to the electrode unit 370. The battery power $V_{battery}$ may be used to determine whether the sensor unit 310 is in contact with the electrode unit 370.

When the sensor unit 310 is connected to the electrode unit 370, the battery power $V_{battery}$ may be supplied to an electrical contact C5 and supplied to the power supply unit 340 through the first conductive member 373 and an electrical contact C4. Accordingly, the signal processing device 300 may determine that the sensor unit 310 is in contact with the electrode unit 370.

The power supply unit 340, in particular, a state determining unit 410 of FIG. 4 described below, may generate a control signal for a power output unit 430 of FIG. 4, for example, a control signal for power output or power cutoff, based on voltage applied to an enable terminal $V_{en}$. The power output unit 430 may supply power to a circuit unit 350 based on the control signal.

Hereinafter, each component of the signal processing device 300 will be described in greater detail.

The sensor unit 310 includes two first electrical contacts C4 and C5 320, at least two second electrical contacts C1, C2, and C3 330, the power supply unit 340, the circuit unit 350, and a battery 360.

The two first electrical contacts C4 and C5 320 may be in contact with the subject directly, or may be in contact with the first conductive member 373 of the electrode unit 370.

The at least two second electrical contacts C1, C2, and C3 330 connected to the circuit unit 350 may be in contact with electrical contacts E1, E2, and E3 connected to at least two second conductive members 376 of the electrode unit 370, respectively.

The power supply unit 340 supplies power to the circuit unit 350 based on whether the two first electrical contacts C4 and C5 320 are in contact with a skin of the subject or the first conductive member 373.

When the two first electrical contacts C4 and C5 320 are in contact with the skin of the subject, the battery power $V_{battery}$ may be supplied to the electrical contact C5 and supplied to the electrical contact C4 through the skin of the subject since a human body is conductive. The battery power $V_{battery}$ supplied to the electrical contact C4 may be supplied to the enable terminal $V_{en}$ of the power supply unit 340. The contact between the two first electrical contacts C4 and C5 320 and the skin of the subject may be used in lieu of a mechanical switch.

Figure 4:
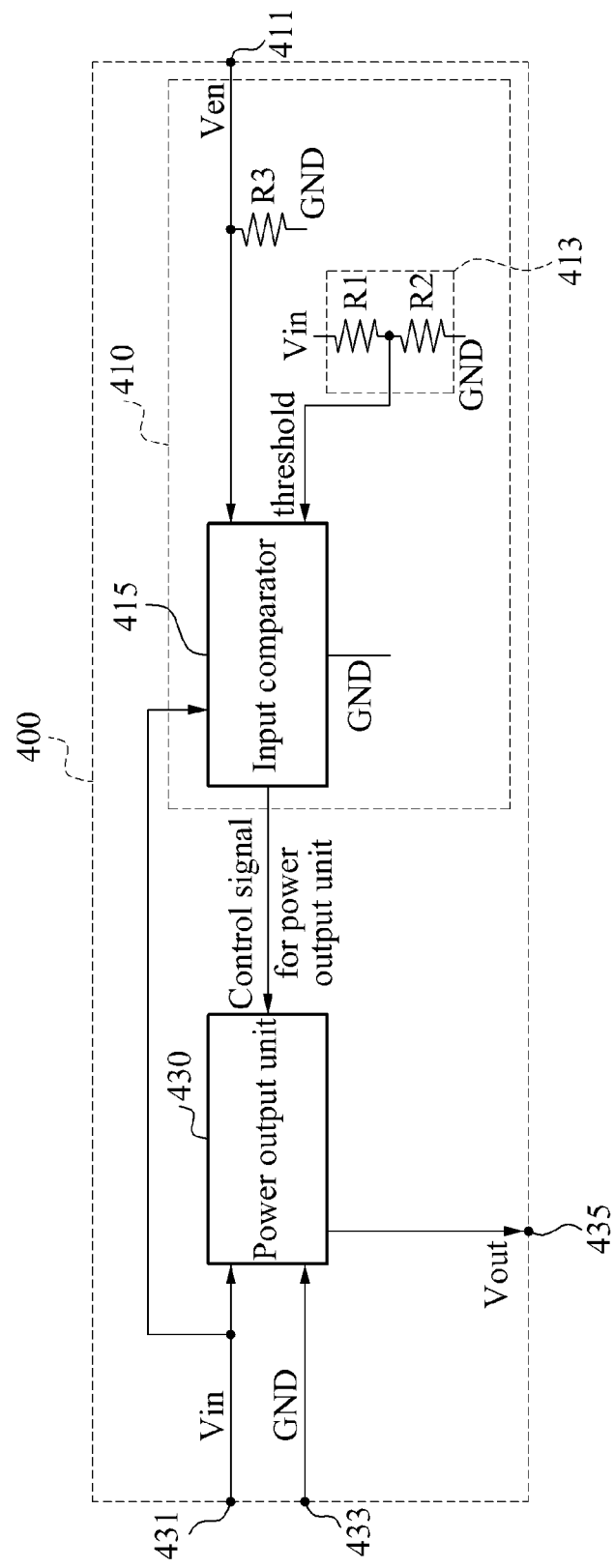
FIG. 4 is a diagram illustrating an example of a power supply unit of the signal processing device of FIG. 3.

The power supply unit 340 generates a control signal for the power output unit 430 of FIG. 4 using the voltage supplied to the enable terminal $V_{en}$ based on whether the two first electrical contacts C4 and C5 320 are in contact with the skin of the subject or the first conductive member 373. The power output unit 430 supplies the battery power $V_{battery}$ input as an input power $V_{in}$ to the circuit unit 350 based on the control signal.

The power supply unit 340 is supplied with an input power $V_{in}$ and a ground power GND from the battery 360. A more detailed description of the power supply unit 340 is provided below with reference to FIGS. 4 through 6.

The circuit unit 350 receives the biometric signal through the at least two second electrical contacts C1, C2, and C3 330 in response to the power supplied from the power supply unit 340, and processes the biometric signal.

The electrode unit 370 includes the first conductive member 373 and the at least two second conductive members 376 disposed to be in contact with at least three regions of the subject.

The first conductive member 373 is disposed to not be in contact with the subject.

An electrical contact E4 connecting together the first electrical contacts C4 and C5 320 of the sensor unit 310 may be formed on the first conductive member 373.

When the sensor 310 is connected to the electrode unit 370, the battery power $V_{battery}$ is supplied to the electrical contact E4 of the electrode unit 370 through the electrical contact C5 of the sensor unit 310 in contact with the electrical contact E4 and supplied to the enable terminal $V_{en}$ of the power supply unit 340 through the electrical contact E4 and the electrical contact C4 of the sensor unit 310 in contact with the electrical contact E4. The electrical contacts E1, E2, and E3 connected to the at least two second conductive members 376 of the electrode unit 370 are in contact with the electrical contacts C1, C2, and C3 of the circuit unit 350.

The signal processing device 300 may receive the biometric signal through the connections between the electrical contacts, process the received biometric signal, and transmit the processing result.

FIG. 4 is a diagram illustrating an example of the power supply unit 340 of the signal processing device 300 of FIG. 3. Referring to FIG. 4, the power supply unit 400 includes a state determining unit 410 and a power output unit 430, and the state determining unit 410 includes an enable terminal $V_{en}$ 411, a voltage divider 413, and an input comparator 415.

The state determining unit 410 generates a control signal for controlling the power supply using voltage supplied based on whether the two first electrical contacts C4 and C5 320 are in contact with the subject or the first conductive member 373. The control signal may be a control signal for controlling the power output unit 430.

The state determining unit 410 compares a voltage or signal input to the enable terminal $V_{en}$ 411 with a predetermined reference voltage or a threshold, and generates and outputs a control signal for controlling the power output unit 430. For example, when the predetermined reference voltage is 0.5V and the input voltage value of the enable terminal $V_{en}$ 411 is 1.8V, the control signal for controlling the power output unit 430 may have a logical high H level.

The logical high H level may represent a high-level voltage value of a digital signal used in the signal processing device, for example, 1.8V in a 0.18 micrometer (µm) complementary metal-oxide-semiconductor (CMOS) process.

The power output unit 430 is supplied with an input power $V_{in}$ 431 and a ground power GND 433 from the battery 360. When the control signal has a logical high H level, the power output unit 430 supplies a required power to an external circuit or the circuit unit 350 through an output terminal $V_{out}$ 435. The voltage value of the output terminal $V_{out}$ 435 may be different from the voltage value $V_{battery}$ of the battery 360.

When a boosting circuit is included in the power supply unit 400, a higher voltage than the battery power $V_{battery}$ may be supplied to the power output unit 430, and when a downconverter is included in the power supply unit 400, a lower voltage than the battery power $V_{battery}$ may be supplied to the power output unit 430.

The input comparator 415 may be supplied with the input power $V_{in}$ 431 from the battery 360 directly, or supplied with power VDD generated by the power output unit 430. A detailed description of the power VDD is provided below with reference to FIG. 5.

The threshold with which the voltage or signal input to the enable terminal $V_{en}$ 411 is to be compared may be generated and provided using various methods. For example, as shown in FIG. 4, the threshold may be set using the voltage divider 413 based on a resistance ratio of resistors R1 and R2. The threshold may be set using a bandgap reference voltage or a voltage generated by flowing a reference current across resistance.

The voltage divider 413 may be supplied with the power $V_{in}$ 431 from the battery 360 directly, or supplied with power VDD generated by the power output unit 430.

The enable terminal $V_{en}$ 411 may be connected to a pull-down resistor R3 connected to the ground power GND.

The pull-down resistor R3 prevents the voltage on the enable terminal $V_{en}$ 411 from floating, and pulls down the voltage on the enable terminal $V_{en}$ 411 to the ground power GND in the absence of an input voltage to the enable terminal $V_{en}$ 411. Also, instead of the pull-down resistor R3, a pull-up resistor may be used.

Figure 5:
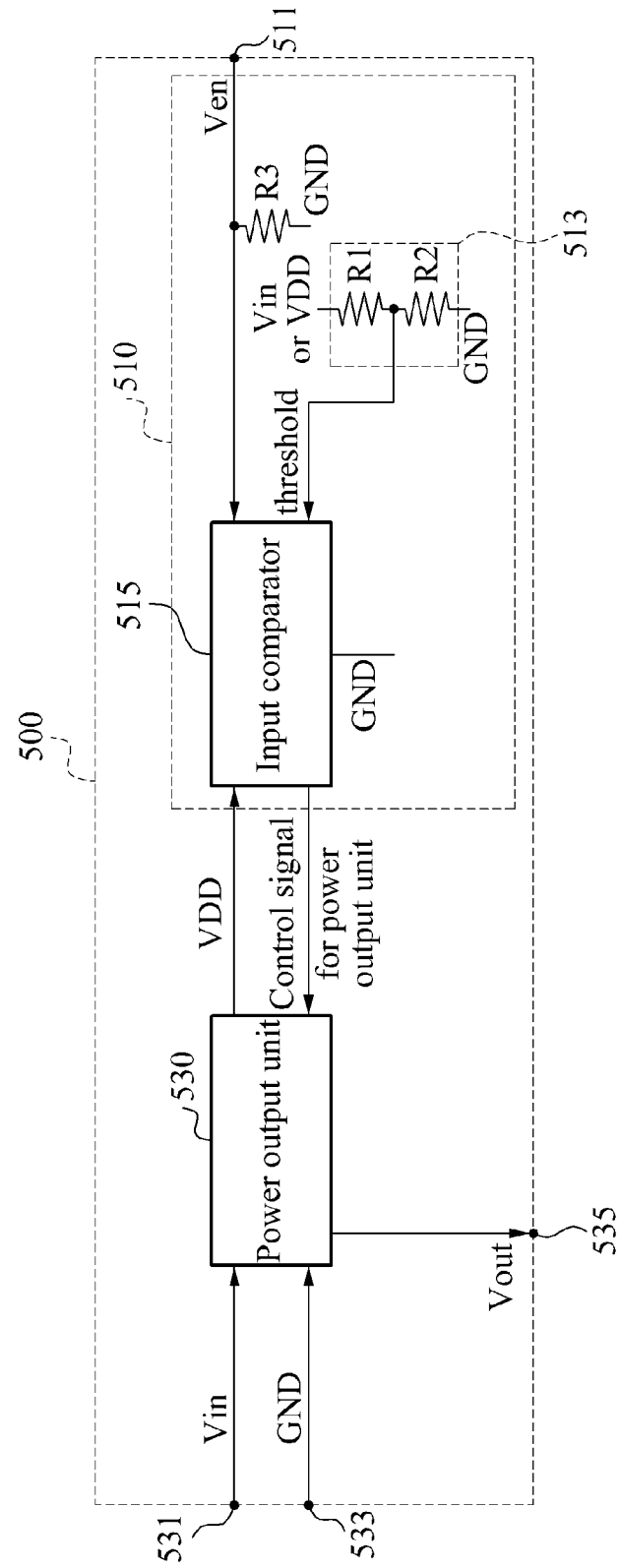
FIG. 5 is a diagram illustrating another example of the power supply unit of the signal processing device of FIG. 3.

FIG. 5 is a diagram illustrating another example of the power supply unit 340 of the signal processing device 300 of FIG. 3. Referring to FIG. 5, the power supply unit 500 includes a state determining unit 510 and a power output unit 530, and the state determining unit 510 includes an enable terminal $V_{en}$ 511, a voltage divider 513, and an input comparator 515.

The input comparator 515 is supplied with power VDD generated by the power output unit 530.

The voltage divider 513 may be supplied with an input power $V_{in}$ 531 from the battery 360 directly, or supplied with power VDD generated by the power output unit 530. The input comparator 515 compares a voltage or a signal input to the enable terminal $V_{en}$ 511 with a threshold generated using the input power $V_{in}$ 531 or the power VDD input to the voltage divider 513.

Since remaining components of the power supply unit 500 are identical to those of FIG. 4, a detailed description thereof will be omitted for conciseness.

Figure 6:
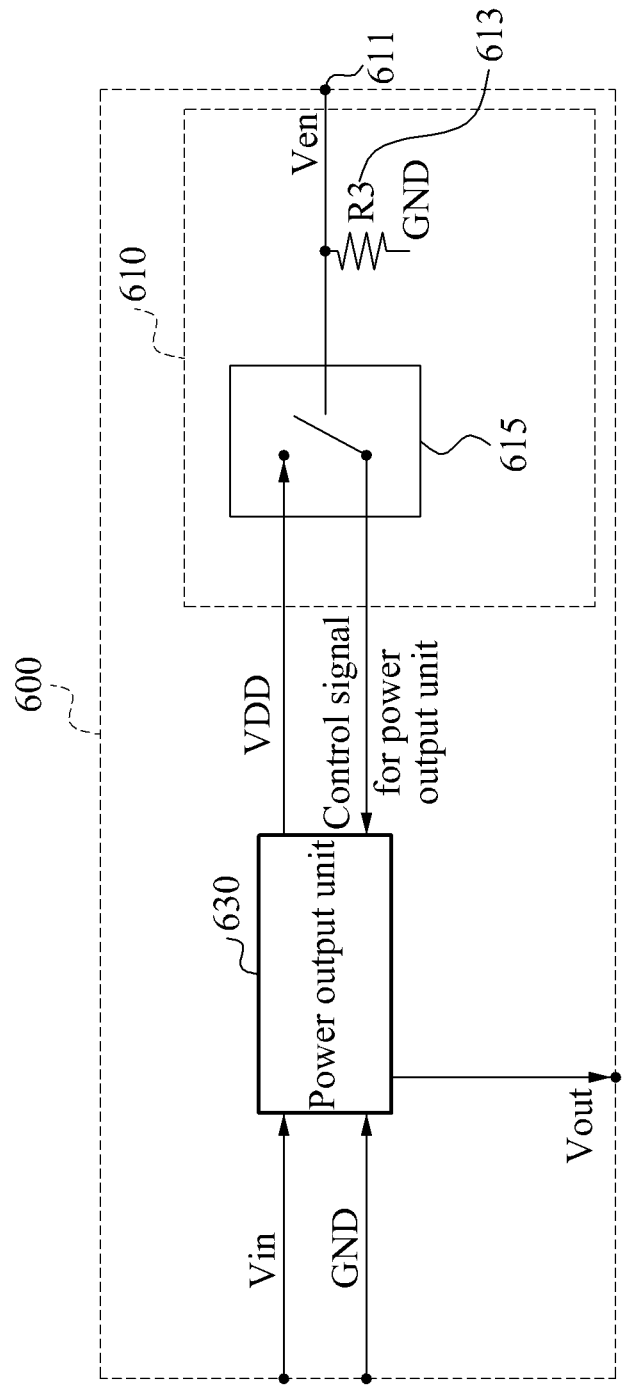
FIG. 6 is a diagram illustrating another example of the power supply unit of the signal processing device of FIG. 3.

FIG. 6 is a diagram illustrating another example of the power supply unit 340 of the signal processing device 300 of FIG. 3. Referring to FIG. 6, the power supply unit 600 includes a state determining unit 610 and a power output unit 630, and the state determining unit 610 includes an enable terminal $V_{en}$ 611, a pull-down resistor R3 613, and a switching unit 615.

The two first electrical contacts C4 and C5 320 of the signal processing device 300 include the electrical contact C5 connected to the battery 360 and the electrical contact C4 connected to the enable terminal $V_{en}$ 611 of the state determining unit 610. The battery power $V_{battery}$ may be supplied to the enable terminal $V_{en}$ 611 of the state determining unit 610 based on whether the electrical contact C5 and the electrical contact C4 are in contact with the subject or the first conductive member 373.

The pull-down resistor R3 613 is connected to the enable terminal $V_{en}$ 611 and a ground power GND to prevent the voltage on the enable terminal $V_{en}$ 611 from floating.

The switching unit 615 generates a control signal for controlling the power output unit 630 to control the power supply to an output terminal $V_{out}$ based on whether the electrical contact C5 and the electrical contact C4 are in contact with the subject or the first conductive member 373. The switching unit 615 may include a metal-oxide-semiconductor (MOS) switch.

Figure 7:
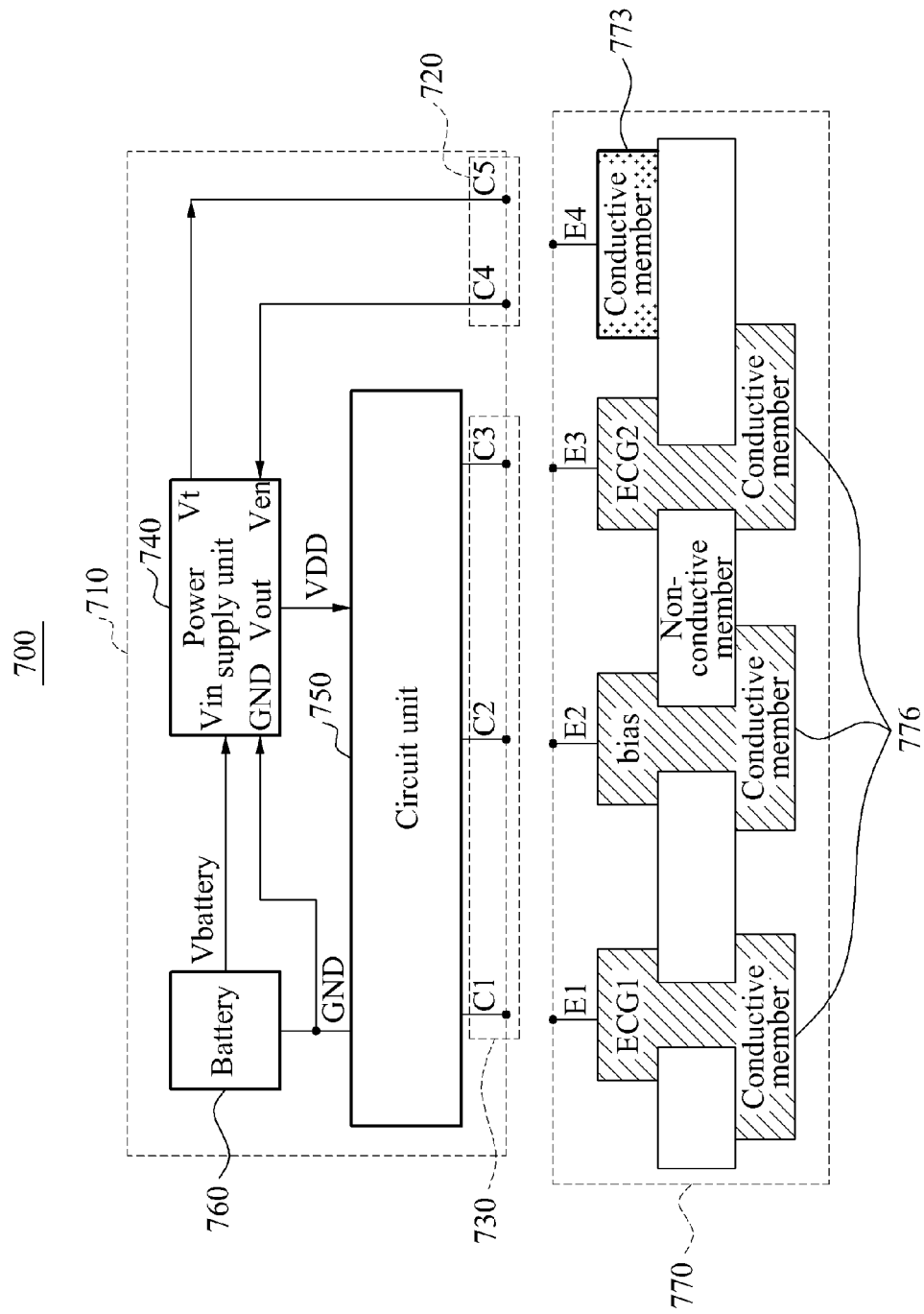
FIG. 7 is a diagram illustrating another example of a signal processing device.

FIG. 7 is a diagram illustrating another example of a signal processing device 700. Referring to FIG. 7, the signal processing device 700 includes a sensor unit 710 and an electrode unit 770.

Similar to the signal processing device 300 in FIG. 3, the signal processing device 700 determines whether the sensor unit 710 is in contact with the electrode unit 770 via a conductive member 773 of the electrode unit 770 when the sensor unit 710 is connected to the electrode unit 770. A separate bias voltage $V_t$ generated by a power supply unit 740 may be used to determine whether the sensor unit 710 is in contact with the electrode unit 770.

When the sensor unit 710 is connected to the electrode unit 770, the bias voltage $V_t$ generated by the power supply unit 740 is supplied to the power supply unit 740 through the conductive member 773. Accordingly, the signal processing device 700 may determine that the sensor unit 710 is in contact with the electrode unit 770.

The power supply unit 740 generates a control signal, for example, a control signal for power output or power cutoff, based on the bias voltage $V_t$ supplied to an enable terminal $V_{en}$. The power supply unit 740 supplies power to a circuit unit 750 based on the control signal.

Hereinafter, each component of the signal processing device 700 will described in greater detail.

The sensor unit 710 includes two first electrical contacts C4 and C5 720, at least two second electrical contacts C1, C2, and C3 730, the power supply unit 740, the circuit unit 750, and a battery 760.

The operation of the power supply unit 740 will be described below with reference to FIG. 8.

Figure 8:
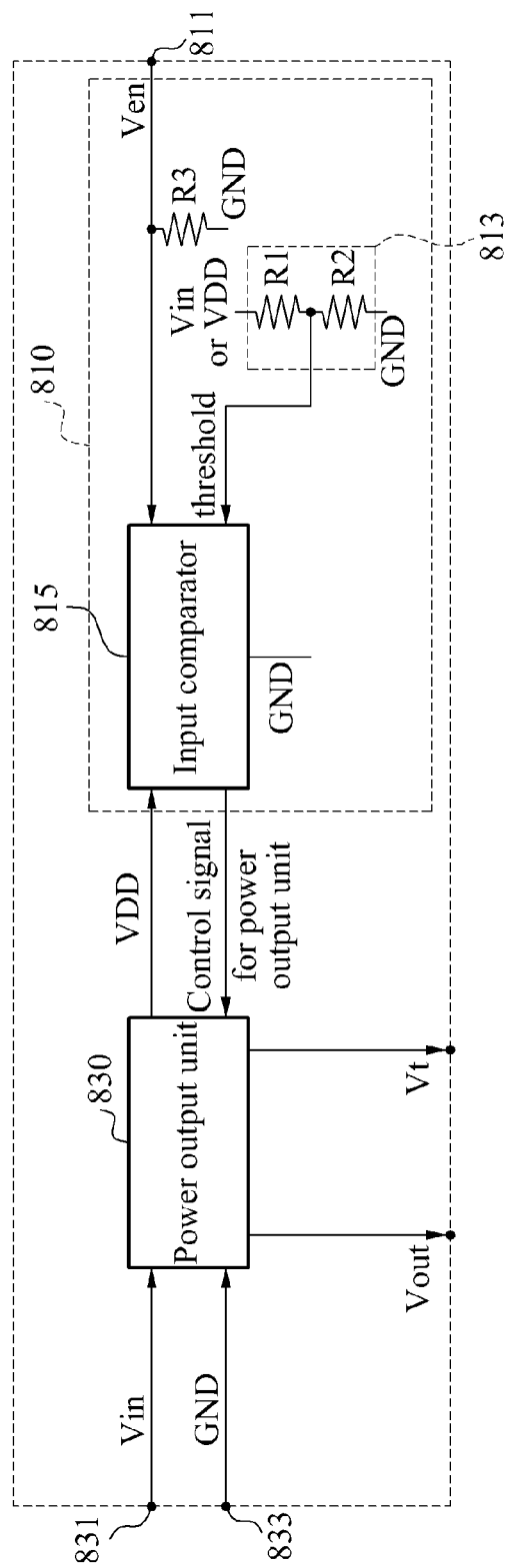
FIG. 8 is a diagram illustrating an example of a power supply unit of the signal processing device of FIG. 7.

FIG. 8 is a diagram illustrating an example of the power supply unit 740 of the signal processing device 700 of FIG. 7. Referring to FIG. 8, a power output unit 830 is supplied with an input power $V_{in}$ and a ground power GND from the battery 760, and provides an output signal $V_t$ to the circuit unit 750. An input comparator 815 is supplied with power VDD output from the power output unit 830, or supplied with power $V_{in}$ from the battery 760 directly.

A state determining unit 810 generates a control signal for controlling the power output unit 830, for example, a control signal for power output or power cutoff, based on a bias voltage $V_t$ supplied to an enable terminal $V_{en}$ 811. The power output unit 830 supplies power to the circuit unit 750 based on the control signal.

The two first electrical contacts C4 and C5 720 include an electrical contact C5 supplied with the separate bias voltage $V_t$ generated by the power output unit 830, and an electrical contact C4 connected to the enable terminal $V_{en}$ 811 of the state determining unit 810.

The separate bias voltage $V_t$ is supplied to the enable terminal $V_{en}$ 811 of the state determining unit 810 based on whether the electrical contact C5 and the electrical contact C4 are in contact with a subject or the first conductive member 773.

The at least two second electrical contacts C1, C2, and C3 730 are disposed to be in contact with electrical contacts E1, E2, and E3 connected to at least two second conductive members 766 through which a biometric signal may be received from the subject.

The circuit unit 750 receives the biometric signal in response to the power supplied from the power supply unit 740, and processes the biometric signal.

The electrode unit 770 includes the first conductive member 773, and the at least two second conductive members 776 disposed to be in contact with at least three regions of the subject through which the biometric signal may be received from the subject.

The first conductive member 773 may be disposed to be not in contact with the subject. An electrical contact E4 of the electrode unit 770 connecting together the first electrical contacts C4 and C5 720 of the sensor unit 710 may be formed on the first conductive member 773.

When the sensor unit 710 is disconnected from the electrode unit 770, the power supply to the electrical contact C4 is interrupted and the ground power GND is supplied to the enable terminal $V_{en}$ of the power supply unit 740 by a pull-down resistor R3 connected to the ground power GND, and the power supply through an output terminal $V_{out}$ of the power supply unit 740 is interrupted.

When the sensor unit 710 is connected to the electrode unit 770, the electrical contacts E1, E2, and E3 connected to the at least two second conductive members 776 of the electrode unit 770 are in contact with the second electrical contacts C1, C2, and C3 of the sensor unit 710, respectively. Also, the first electrical contacts C4 and C5 are in contact with the electrical contact E4.

When the first electrical contacts C4 and C5 are in contact with the electrical contact E4, a higher voltage than a threshold voltage is applied to the enable terminal $V_{en}$ of the power supply unit 740. When the control signal for controlling the power output unit 830 of the power supply unit 740 has a high level H, the power supply unit 740 supplies power to the circuit unit 750 through the output terminal $V_{out}$.

A voltage divider 813 may be supplied with an input power $V_{in}$ 831 from the battery 760 directly, or supplied with power VDD generated by the power output unit 830. The input comparator 815 compares a voltage or a signal input to the enable terminal $V_{en}$ 811 with a threshold generated using the input power $V_{in}$ 831 or the power VDD input to the voltage divider 813.

The signal processing device 700 may allow direct contact of the sensor unit 710 with the subject to eliminate the need for the electrode unit 770.

Hereinafter, a signal processing device without an electrode unit will be described.

Figure 9:
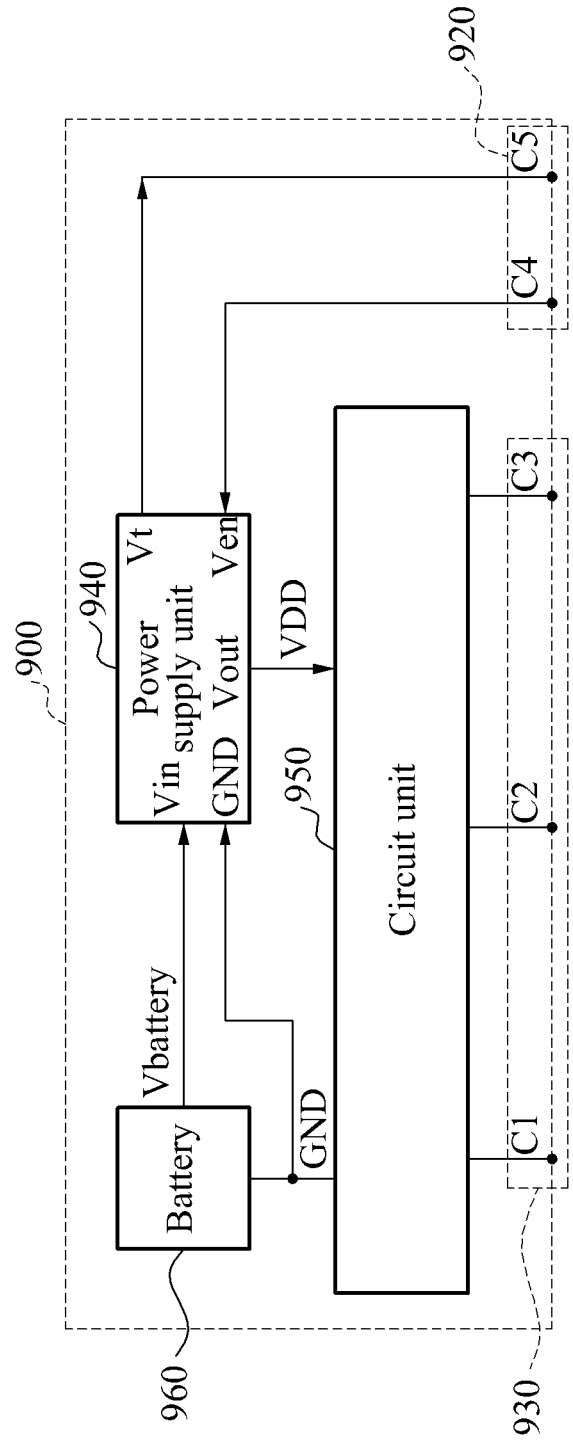
FIG. 9 is a diagram illustrating an example of signal processing device without an electrode unit.

FIG. 9 is a diagram illustrating an example of a signal processing device 900 without an electrode unit. Referring to FIG. 9, the signal processing device 900 includes a sensor unit alone, and the sensor unit may be identical to the sensor unit 710 of FIG. 7. The signal processing device 900 includes two first electrical contacts C4 and C5 920, at least two second electrical contacts C1, C2, and C3 930, a power supply unit 940, a circuit unit 950, and a battery 960.

The at least two second electrical contacts C1, C2, and C3 930 are connected to the circuit unit 950. The two first electrical contacts C4 and C5 920 are connected to an enable terminal $V_{en}$ of the power supply unit 940 and a terminal supplied with a separate bias voltage $V_t$ generated by the power supply unit 940, respectively.

The at least two second electrical contacts C1, C2, and C3 930 and the two first electrical contacts C4 and C5 920 may form electrical contacts with different regions of a subject.

When the two first electrical contacts C4 and C5 920 are in contact with a skin of the subject, the bias voltage $V_t$ is supplied to the electrical contact C5 and supplied to the electrical contact C4 through the skin of the subject since a human body is conductive. A predetermined resistance or impedance may be formed between the two first electrical contacts C4 and C5 920. The bias voltage $V_t$ supplied to the electrical contact C4 is supplied to the enable terminal $V_{en}$ of the power supply unit 940.

The bias voltage $V_t$ is supplied to the power supply unit 940 through the two first electrical contacts C4 and C5 920 forming electrical contacts with different regions of the subject. Contact between the two first electrical contacts C4 and C5 920 and the skin of the subject enables power to be supplied to the circuit unit 950 without using a mechanical switch.

Figure 10:
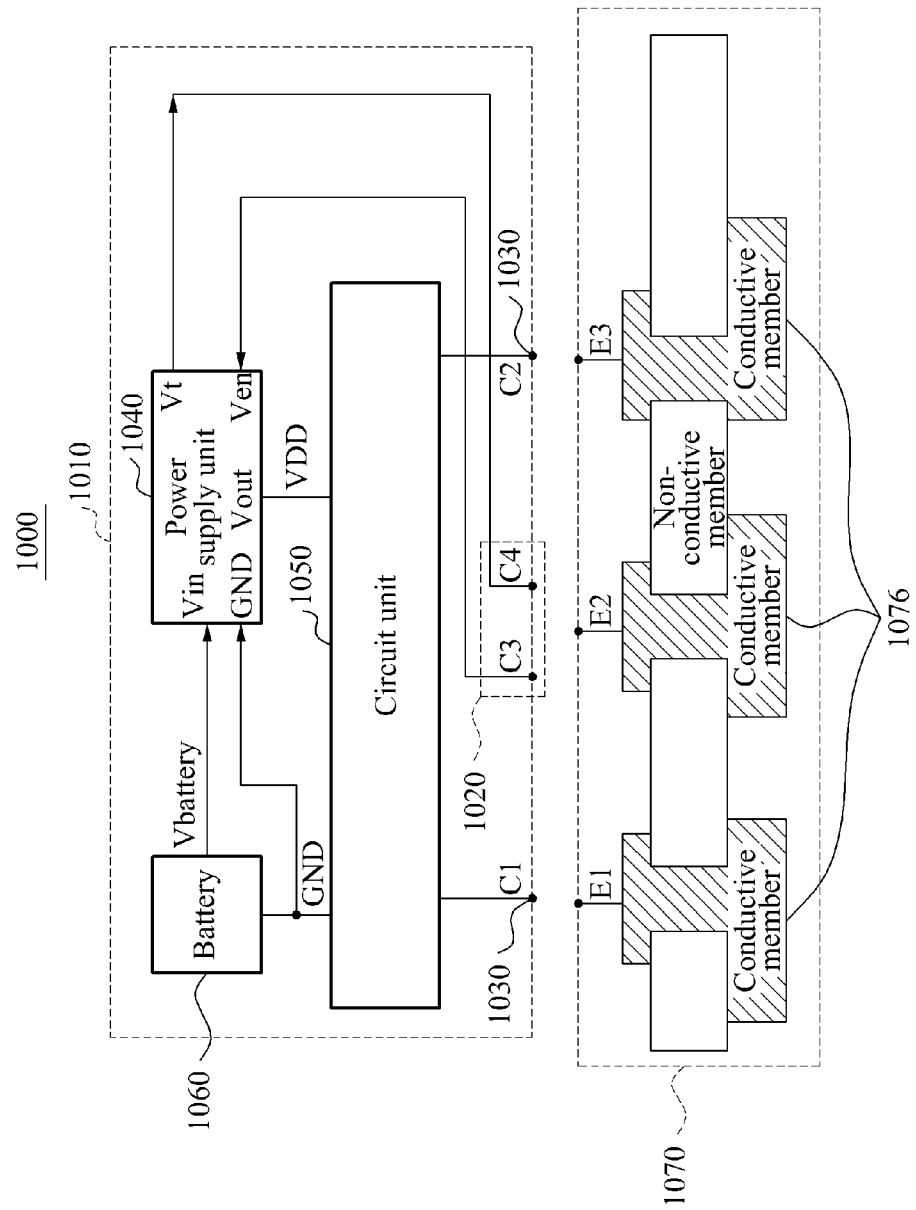
FIG. 10 is a diagram illustrating another example of a signal processing device.

FIG. 10 is a diagram illustrating another example a signal processing device 1000. Referring to FIG. 10, the signal processing device 1000 includes a sensor unit 1010 and an electrode unit 1070.

The sensor unit 1010 may be connected to the electrode unit 1070, and one surface of the electrode unit 1070, for example, conductive members 1076 of the electrode unit 1070, may be attached to a subject.

When electrical contacts C1, C2, C3, and C4 of the sensor unit 1010 are disconnected from the electrode unit 1070 or the subject, a ground power GND is applied to an enable terminal $V_{en}$ of a power supply unit 1040, for example, by a pull-down resistor connected to the ground power GND, similar to the pull-down resistor R3 of FIG. 8. A control signal for controlling a power output unit (refer to the power output unit 830 of FIG. 8) may have an L value or a GND value to interrupt a power supply to an output terminal $V_{out}$ of the power output unit.

Unlike the signal processing device 300 of FIG. 3 and the signal processing device 700 of FIG. 7, the signal processing device 1000 may use one of the conductive members 1076 of the electrode unit 1070 to establish a connection between the electrical contacts C3 and C4.

The sensor unit 1010 includes two first electrical contacts C3 and C4 1020, at least two second electrical contacts C1 and C2 1030, the power supply unit 1040, a circuit unit 1050, and a battery 1060.

The electrode unit 1070 includes at least two conductive members 1076 disposed to be in contact with at least three regions of the subject.

The at least two second electrical contacts C1 and C2 1030 connected to the circuit unit 1050 may be in contact with electrical contacts E1 and E3 of the electrode unit 1070 through which a biometric signal may be received from the subject.

The two first electrical contacts C3 and C4 1020 include the electrical contact C4 supplied with the separate bias voltage $V_t$ generated by the power supply unit 1040, and the electrical contact C3 connected to the enable terminal $V_{en}$ of the power supply unit 1040. The bias voltage $V_t$ is supplied to the enable terminal $V_{en}$ based on whether the electrical contact C4 and the electrical contact C3 are in contact with an electrical contact E2 of the electrode unit 1070 connected to one of the conductive members 1076. The first electrical contacts C3 and C4 1020 may be connected together by the electrical contact E2 connected to the one of the conductive members 1076.

Similar to the signal processing device 800 of FIG. 8, the signal processing device 1000 may enable the power supply to the circuit unit 1050 through direct contact with the skin of the subject without the electrode unit 1070.

To ensure a robust operation of the sensor unit 1010, the power supply to the circuit unit 1050 may be cut off when the circuit unit 1050 and the electrode unit 1070 are disconnected, or when the circuit unit 1050 and the subject are disconnected.

To prevent the power supply from being cut off due to a temporary non-contact state, a state determining unit (not shown, but similar to the state determining unit 810 of FIG. 8) of the power supply unit 1040 may determine whether a non-contact time between the electrical contacts C3 and C4 is longer than or equal to a predetermined period of time, for example, 1 millisecond (ms). When the non-contact time between the electrical contacts C3 and C4 is less than the predetermined period of time, the power supply to the circuit unit 1050 may be continued. When the non-contact time between the electrical contacts C3 and C4 is longer than or equal to the predetermined period of time, the power supply to the circuit unit 1050 may be cut off.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A signal processing device, comprising:
a detection unit configured to detect an intent to use the signal processing device based on a determination of whether the signal processing device is in electrical contact with a subject, the detection unit comprising two first electrical contacts; and
a power supply unit configured to supply power to operate the signal processing device based on the detected intent and generate a bias voltage separate from the power, the power supply unit comprises an enable terminal; and
wherein the detection unit is configured to perform the determining of whether the signal processing device is in electrical contact with the subject by supplying a first voltage of the bias voltage to one of the two first electrical contacts and sensing a second voltage from another of the two first electrical contacts, and when the determination indicates that the signal processing device is in electrical contact with the subject the two first electrical contacts are contacting one of the subject and a first conductive member of a biometric electrode unit,
wherein the another of the two first electrical contacts is connected to the enable terminal,
wherein the power supply unit is configured to maintain the supplied power during a predetermined threshold after the detection unit no longer detects that the signal processing device is in electrical contact with the subject.

2. The signal processing device of claim 1, wherein:
the power supply unit is further configured to supply the power to operate the signal processing device based on whether the two first electrical contacts are in electrical contact with the subject or the first conductive member of the biometric electrode unit; and
the signal processing device further comprises a circuit unit configured to receive a biometric signal from the subject in response to the power to operate the signal processing device supplied by the power supply unit, and process the biometric received signal.

3. The signal processing device of claim 2, further comprising the biometric electrode unit arranged to electrically contact with the subject, the electrode unit comprising:
the first conductive member; and
at least two second conductive members, of a plurality of second conductive members arranged to electrically contact with at least three separate regions of the subject, to receive the biometric signal from the subject.

4. The signal processing device of claim 3, wherein the electrode unit further comprises contacts connected to the at least two second conductive members to receive the biometric signal from the subject from the at least two second conductive members; and
at least two second electrical contacts arranged to electrically contact the contacts connected to the at least two second conductive members to receive the biometric signal from the subject from the contacts connected to the at least two second conductive members when the signal processing device is in contact with the subject.

5. The signal processing device of claim 3, wherein the first conductive member is configured to not to be in contact with the subject when the electrode unit is in contact with the subject.

6. The signal processing device of claim 3, wherein the power supply unit further comprises;
the first conductive member is one of the at least two second conductive members;
the electrode unit further comprises a contact connected to the one of the at least two second conductive members that is the first conductive member.

7. The signal processing device of claim 2, wherein the power supply unit comprises:
a state determining unit configured to generate a control signal for controlling the power supply based on a voltage supplied to the state determining unit based on whether the two first electrical contacts are in contact with the subject or the first conductive member; and
a power output unit configured to receive battery power from a battery, generate the power to operate the signal processing device based on the battery power, and selectively supply the power to operate the signal processing device to the circuit unit based on the control signal; and
the power to operate the signal processing device generated by the power output unit is the battery power or a power having a voltage that is different from a voltage of the battery power.

8. The signal processing device of claim 7, wherein the state determining unit comprises:
an enable terminal configured to receive the voltage supplied to the state determining unit;
a switching unit configured to generate a control signal for controlling the power supply based on the voltage received by the enable terminal based on whether the two first electrical contacts are in contact with the subject or the first conductive member; and
a pull-down resistor connected to the enable terminal to prevent a voltage on the enable terminal from floating.

9. The signal processing device of claim 8, wherein the at least two first electrical contacts comprise:
a first contact connected to the battery; and
a second contact connected to the enable terminal of the state determining unit; and
the battery power is supplied from the battery to the enable terminal of the state determining unit based on whether the first contact and the second contact are in contact with the subject or the first conductive member.

10. The signal processing device of claim 8, wherein the power output unit is further configured to generate a bias voltage separate from the battery power;
the at least two first electrical contacts comprise:
a first contact supplied with the bias voltage; and
a second contact connected to the enable terminal of the state determining unit; and
the bias voltage is supplied to the enable terminal of the state determining unit based on whether the first contact and the second contact are in contact with the subject or the first conductive member.

11. The signal processing device of claim 8, wherein the state determining unit comprises:
an enable terminal configured to receive the voltage supplied to the state determining unit;

an input comparing unit configured to generate the control signal by comparing the voltage received by the enable terminal with a threshold voltage based on whether the two first electrical contacts are in contact with the subject or the first conductive member; and a threshold voltage generating unit comprising a voltage divider having a resistance ratio, the threshold voltage generating unit being configured to generate the threshold voltage based on the resistance ratio of the voltage divider.

12. The signal processing device of claim 11, wherein the two first electrical contacts comprise:
a first contact connected to the battery; and
a second contact connected to the enable terminal of the state determining unit; and
the power is supplied from the battery to the enable terminal of the state determining unit based on whether the first contact and the second contact are in contact with the subject or the first conductive member.

13. The signal processing device of claim 11, wherein the two first electrical contacts comprise:
a first contact configured to receive the bias voltage generated by the power output unit; and
a second contact connected to the enable terminal of the state determining unit; and
the bias voltage is supplied to the enable terminal of the state determining unit based on whether the first contact and the second contact are in contact with the subject or the first conductive member.

14. The signal processing device of claim 11, wherein the voltage divider is configured to receive the battery power from the battery, or the power to operate the signal processing device from the power output unit.

15. The signal processing device of claim 11, further comprising a pull-down resistor or a pull-up resistor connected to the enable terminal to prevent a voltage on the enable terminal from floating.

16. The signal processing device of claim 1, wherein the power supply unit is further configured to receive an input power and a ground power from a battery.

17. The signal processing device of claim 1, wherein the detection unit is further configured to perform the determining of whether the signal processing device is in electrical contact with the subject based on the one of the first two electrical contacts and the another of the two first electrical contacts being electrically connected through a first conductive member that is not in contact with a subject.

18. A signal processing device, comprising:
a biometric electrode unit comprising:
a first conductive member configured to not be in contact with a subject when the biometric electrode unit is in contact with the subject; and
at least two second conductive members, of a plurality of second conductive members arranged to electrically contact at least three separate regions of the subject, to receive a biometric signal from the subject;
two first electrical contacts arranged to electrically contact with the first conductive member; and
a circuit unit configured to receive a signal through one of the two first electrical contacts in response to power supplied to another of the two first electrical contacts from a battery based on whether the other of the two first electrical contacts is in contact with the first conductive member, and process the received signal; and
a detection unit configured to detect an intent to use the signal processing device based on the received signal,
wherein the battery supplies a bias voltage separate from the power to one of the two first electrical contacts and the circuit unit receives the signal by using the power supplied to the another of the two first electrical contacts,
wherein the power is maintained during a predetermined threshold after the detection unit no longer detects the intent to use the signal processing device based on the received signal.

19. The signal processing device of claim 18, wherein the two first electrical contacts comprise:
a first contact connected to the battery; and
a second contact connected to the circuit unit; and
the power is supplied to the circuit unit from the battery by contacting between the first contact and one of the first conductive member and the subject.

* * * * *